US00PP22268P2

(12) United States Plant Patent
Tas

(10) Patent No.: US PP22,268 P2
(45) Date of Patent: Nov. 22, 2011

(54) ***ALSTROEMERIA* PLANT NAMED 'TESNAVA'**

(50) Latin Name: *Alstroemeria hybrida*
Varietal Denomination: Tesnava

(75) Inventor: Marius Tas, De Kwakel (NL)

(73) Assignee: VOF Hortipartners, Heerhugowaard (NL)

( * ) Notice: Subject to any disclaimer, the term of this patent is extended or adjusted under 35 U.S.C. 154(b) by 0 days.

(21) Appl. No.: 13/134,175

(22) Filed: May 31, 2011

(51) Int. Cl.
*A01H 5/00* (2006.01)

(52) U.S. Cl. ..... Plt./309

(58) Field of Classification Search ..... Plt./309
See application file for complete search history.

(56) References Cited

U.S. PATENT DOCUMENTS

PP14,131 P2 * 9/2003 Hoogendoorn ..... Plt./309
PP20,976 P2 * 5/2010 Konst ..... Plt./309

OTHER PUBLICATIONS

UPOV ROM GTITM Computer Database, GTI Jouve Retrieval Software 2011/01 Citation for 'Tesnava'.*

* cited by examiner

*Primary Examiner* — Wendy C Haas
(74) *Attorney, Agent, or Firm* — C. A. Whealy

(57) ABSTRACT

A new and distinct cultivar of *Alstroemeria* plant named 'Tesnava', characterized by its compact and uniformly mounding plant habit; sturdy and strong plants; moderately vigorous growth habit; purple and white bi-colored flowers with short pedicels; and good garden performance.

1 Drawing Sheet

Botanical designation: *Alstroemeria hybrida.*
Cultivar denomination: 'TESNAVA'.

BACKGROUND OF THE INVENTION

The present invention relates to a new and distinct cultivar of *Alstroemeria* plant, botanically known as *Alstroemeria hybrida*, grown typically as a potted garden *Alstroemeria*, and hereinafter referred to by the name 'Tesnava'.

The new *Alstroemeria* plant is a product of a planned breeding program conducted by the Inventor in De Kwakel, The Netherlands. The objective of the breeding program is to create new potted garden *Alstroemeria* plants that flower continuously and have attractive leaf and flower coloration.

The new *Alstroemeria* plant originated from a cross-pollination made by the Inventor in De Kwakel, The Netherlands in April, 2006, of a proprietary *Alstroemeria hybrida* selection identified as code number Pa920, not patented, as the female, or seed, parent with a proprietary *Alstroemeria hybrida* selection identified as code number Pa1819, not patented, as the male, or pollen, parent. The new *Alstroemeria* plant was discovered and selected by the Inventor as a single flowering plant from within the progeny of the stated cross-pollination in a controlled greenhouse environment in De Kwakel, The Netherlands in April, 2007.

Asexual reproduction of the new *Alstroemeria* plant by root divisions in a controlled greenhouse environment in. De Kwakel, The Netherlands since May, 2007 has shown that the unique features of this new *Alstroemeria* plant are stable and reproduced true to type in successive generations.

SUMMARY OF THE INVENTION

Plants of the new *Alstroemeria* have not been observed under all possible environmental conditions and cultural practices. The phenotype may vary somewhat with variations in environment conditions such as temperature and light intensity without, however, any variance in genotype.

The following traits have been repeatedly observed and are determined to be the unique characteristics of 'Tesnava'. These characteristics in combination distinguish 'Tesnava' as a new and distinct *Alstroemeria* plant:

1. Compact and uniformly mounding plant habit.
2. Sturdy and strong plants; moderately vigorous growth habit.
3. Purple and white bi-colored flowers with short pedicels.
4. Good garden performance.

Plants of the new *Alstroemeria* can be compared to plants of the female parent selection. Plants of the new *Alstroemeria* differ from plants of the female parent selection in the following characteristics:

1. Plants of the new *Alstroemeria* are shorter than plants of the female parent selection.
2. Plants of the new *Alstroemeria* and the female parent selection differ in flower bud color as plants of the female patent selection have lavender green-colored flower buds.
3. Plants of the new *Alstroemeria* and the female parent selection differ in flower color as plants of the female patent selection have pink and white bi-colored flowers.
4. Plants of the new *Alstroemeria* have shorter pedicels than plants of the female parent selection.

Plants of the new *Alstroemeria* can be compared to plants of the male parent selection. Plants of the new *Alstroemeria* differ from plants of the male parent selection in the following characteristics:

1. Plants of the new *Alstroemeria* are shorter than plants of the male parent selection.
2. Plants of the new *Alstroemeria* and the male parent selection differ in flower bud color as plants of the male patent selection have light pinkish green-colored flower buds.

3. Plants of the new *Alstroemeria* and the male parent selection differ in flower color as plants of the male patent selection have white and blushed pink-colored flowers.

Plants of the new *Alstroemeria* can be compared to plants of the *Alstroemeria hybrida* 'Staprivane' disclosed in U.S. Plant Pat. No. 14,131. In side-by-side comparisons, plants of the new *Alstroemeria* differed primarily from plants of 'Staprivane' in the following characteristics:

1. Plants of the new *Alstroemeria* and 'Staprivane' differed in flower bud color as plants of 'Staprivane' had purple-colored flower buds.
2. Plants of the new *Alstroemeria* and 'Staprivane' differed in flower color as plants of 'Staprivane' had purple and yellow bi-colored flowers.
3. Plants of the new *Alstroemeria* had shorter pedicels than plants of 'Staprivane'.

BRIEF DESCRIPTION OF THE PHOTOGRAPH

The accompanying colored photograph illustrates the overall appearance of the new *Alstroemeria* plant showing the colors as true as it is reasonably possible to obtain in colored reproductions of this type. Colors in the photograph may differ slightly from the color values cited in the detailed botanical description which accurately describe the colors of the new *Alstroemeria* plant. The photograph comprises a side perspective view of a typical flowering plant of 'Tesnava' grown in a container.

DETAILED BOTANICAL DESCRIPTION

The aforementioned photograph and following observations and measurements describe plants of the new *Alstroemeria* grown in 4.6-liter containers during the winter in a glass-covered greenhouse in De Kwakel, The Netherlands. During the production of the plants, day and night temperatures ranged from 18° C. to 22° C. Plants were 15 weeks old when the photograph and description were taken. Color references are made to The Royal Horticultural Society Colour Chart, 2007 Edition, except where general terms of ordinary dictionary significance are used.

Botanical classification: *Alstroemeria hybrida* 'Tesnava'.

Parentage:

*Female, or seed, parent.*—Proprietary *Alstroemeria hybrida* selection identified as code number Pa920, not patented.

*Male or pollen parent.*—Proprietary *Alstroemeria hybrida* selection identified as code number Pa1819, not patented.

Propagation:

*Type.*—By root divisions.

*Time to produce a rooted young plant, summer.*—About seven weeks at 20° C.

*Time to produce a rooted young plant, winter.*—About eight weeks at 16° C.

*Root description.*—Fibrous, fleshy; up to 2 cm in thickness; white in color.

*Rooting habit.*—Freely branching; medium density.

Plant description:

*Plant and growth habit.*—Compact and uniformly mounded habit; freely branching habit, dense and bushy appearance; sturdy and strong plants; moderately vigorous growth habit.

*Plant height.*—About 23.1 cm.

*Plant diameter* (*area of spread*).—About 33.5 cm.

Stem description:

*Aspect.*—Mostly upright to somewhat outwardly spreading.

*Length.*—About 10.3 cm.

*Diameter.*—About 7 mm.

*Internode length.*—About 5 mm.

*Strength.*—Moderately strong.

*Texture.*—Smooth, glabrous.

*Color.*—Close to 144A with a thin dull outer layer, closer to 145A.

Foliage description:

*Arrangement.*—Alternate; below the peduncles in a single whorl; simple.

*Length.*—About 6.1 cm.

*Width.*—About 2.8 cm.

*Shape.*—Narrowly ovate to lanceolate.

*Apex.*—Acute.

*Base.*—Long and narrowly cuneate.

*Margin.*—Entire.

*Texture, upper and lower surfaces.*—Smooth, glabrous.

*Venation pattern.*—Parallel.

*Color.*—Developing leaves, upper surface: Close to 137B. Developing leaves, lower surface: Close to N137A. Fully expanded leaves, upper surface: Close to 137C; venation, close to 137C. Fully expanded leaves, lower surface: Close to N137A; venation, close to N137A.

*Petioles.*—Length: About 2.5 cm. Diameter: About 1 mm. Color: Close to 143A.

Flower description:

*Flower type and habit.*—Single cup-shaped flowers arranged in compound umbels; flowers face mostly outwardly; perianth segments separate; freely flowering habit with about 20 flowers per inflorescence and about 140 flowers developing per plant.

*Natural flowering season.*—Plants begin flowering about seven weeks after planting; flowering continuous from early April through the summer in The Netherlands.

*Fragrance.*—None detected.

*Flower longevity on the plant.*—About ten days; flowers not persistent.

*Flower buds.*—Length: About 3.4 cm. Diameter: About 1.4 cm. Shape: Obovate. Color: Proximal half, close to 145C to 145D; distal, close to 143A to 143B.

*Umbel height.*—About 10.5 cm.

*Umbel diameter.*—About 16 cm.

*Flower diameter.*—About 7.5 cm by 7.2 cm.

*Flower depth* (*height*).—About 6.1 cm.

*Perianth.*—Arrangement: Six arranged in two whorls, each whorl with two lateral and one median segments. Size, inner perianth: Length, lateral segments: About 6.5 cm. Width, lateral segments: About 2.3 cm. Length, median segment: About 5.4 cm. Width, median segment: About 2.2 cm. Size, outer perianth: Length, all segments: About 5.9 cm. Width, all segments: About 3.7 cm. Shape, inner perianth, lateral and median segments: Narrowly obovate. Shape, outer perianth, lateral and median segments: Obcordate. Apex, inner perianth, lateral and median segments: Abruptly acute. Apex, outer perianth, lateral and median segments: Broadly retuse with a small abruptly acute point. Base, inner and outer perianths, lateral and median segments: Attenuate or cuneate. Margin, inner and outer perianths, lateral and median segments: Entire. Texture, inner and outer perianths, lateral and median segments: Smooth, glabrous. Color, inner perianth: When opening, all segments, upper surface: Close to 77B; apex, close to 146B; center, close to 4D; towards the base, close to 158D; spots and streaks, close to 187A. When opening, all segments, lower surface: Close to 77C; apex, close to 146B; center, close to 75B to 75C; central band, close to 72A to 72B; towards the base, between 75A and 77C; spots and streaks, close to 197C to 197D. Fully opened, all segments, upper surface: Close to 77B; apex, close to 146B; center, close to 4D; towards the base, close to 158D; spots and streaks, close to 187A; color does not change with development. When opening, all segments, lower surface: Close to 77C; apex, close to 146B; center, close to 150C to 150D; central band, close to 72B; towards the base, close to 182C to 182D; spots and streaks, close to 197A to 197B; color does not change with development. Color, outer perianth: When opening, all segments, upper surface: Close to 77A; apex, close to 146A to 146B; towards the base, close to 77D. When opening, all segments, lower surface: Close to 77B; large blotch and apex, close to 147B; towards the base, close to 77C. Fully opened, all segments, upper surface: Close to 76A; apex, close to 146B; towards the base, close to 76B to 76C; color does not change with development. Fully opened, all segments, lower surface: Close to 76A; large blotch and apex, close to 137C; towards the base, close to 76B; color does not change with development.

*Pedicels.*—Length: About 1.5 cm. Diameter: About 2 mm. Strength: Moderately strong. Angle: Erect to about 30° from vertical. Texture: Smooth, glabrous. Color: Close to 143B.

*Reproductive organs.*—Stamens: Quantity per flower: Six. Filament length: About 3.4 cm. Filament color: Close to 75A; towards the base, close to 75D. Anther shape: Oblong to elliptical. Anther length: About 7 mm. Anther color: Close to 152D. Pollen amount: Moderate. Pollen color: Darker than between 122A and 202B. Pistils: Quantity per flower: One. Pistil length: About 4.2 cm. Style length: About 3.7 cm. Style color: Close to 76B to 76C; towards the base, close to 144C. Stigma shape: Tri-parted; parts, club-shaped, curved. Stigma color: Close to 76C to 76D. Ovary color: Close to 138B.

*Fruit/seed.*—Fruit and seed development has not been observed on plants of the new *Alstroemeria*.

Disease/pest resistance: Plants of the new *Alstroemeria* have not been observed to be resistant to pathogens and pests common to *Alstroemeria*.

Garden performance: Plants of the new *Alstroemeria* have been observed to have good garden performance and to tolerate wind and rain. Plants of the new *Alstroemeria* have been observed to tolerate high temperatures of about 35° C. and to be hardy to USDA Hardiness Zone 8.

It is claimed:

1. A new and distinct *Alstroemeria* plant named 'Tesnava' as illustrated and described.

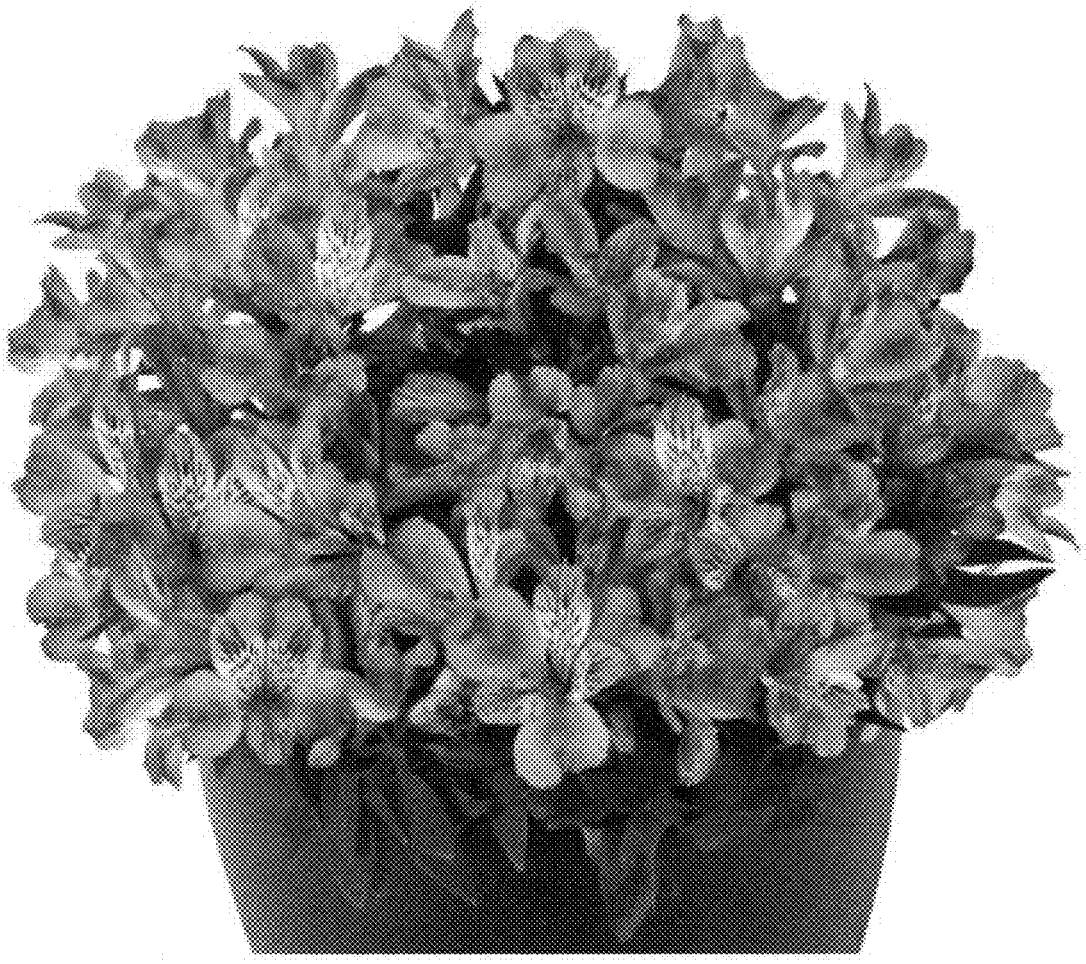

* * * * *